US009993169B2

(12) United States Patent
Kotanko et al.

(10) Patent No.: US 9,993,169 B2
(45) Date of Patent: Jun. 12, 2018

(54) METHOD AND APPARATUS OF ASSESSMENT OF ACCESS FLOW IN HEMODIALYSIS PATIENTS BY VIDEO IMAGING PROCESSING

(71) Applicant: FRESENIUS MEDICAL CARE HOLDINGS, INC., Waltham, MA (US)

(72) Inventors: Peter Kotanko, New York, NY (US); Fansan Zhu, Flushing, NY (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 43 days.

(21) Appl. No.: 15/340,490

(22) Filed: Nov. 1, 2016

(65) Prior Publication Data

US 2017/0119258 A1    May 4, 2017

Related U.S. Application Data

(60) Provisional application No. 62/250,294, filed on Nov. 3, 2015.

(51) Int. Cl.
*G06K 9/00* (2006.01)
*A61B 5/026* (2006.01)
(Continued)

(52) U.S. Cl.
CPC ............ *A61B 5/0261* (2013.01); *A61B 5/702* (2013.01); *A61M 1/14* (2013.01); *A61M 1/3656* (2014.02);
(Continued)

(58) Field of Classification Search
CPC .......... G06T 7/0012; G06T 7/20; G06T 7/00; G06T 7/254; G06T 7/0016; G06T 2207/30004; G06T 2207/10016; G06T 2207/10021; G06T 2207/10056; G06T 2207/30101; G06T 2207/30104; G06T 2210/41; G06K 9/00496;
(Continued)

(56) References Cited

U.S. PATENT DOCUMENTS 6,692,443 B2    2/2004 Crutchfield et al.
9,842,404 B2 *  12/2017 Freeman ................... G06T 7/20
(Continued)

OTHER PUBLICATIONS

International Search Report and Written Opinion of the International Searching Authority from corresponding PCT/US2016/059885 dated Mar. 10, 2017.

*Primary Examiner* — Jose Couso
(74) *Attorney, Agent, or Firm* — Lando & Anastasi, LLP

(57) ABSTRACT

Systems and methods are provided for assessing patient blood flow using video image processing. According to one aspect, a method of analyzing at least one blood flow characteristic of a patient includes capturing a video including a plurality of frames of an arterio-venous (AV) fistula on the patient; amplifying motion in the video to produce a motion-amplified video; determining a difference in intensity between consecutive frames in the motion-amplified video to produce a time-function of an amplitude of the optic flow representing movement in an area of interest on the patient; and determining the at least one blood flow characteristic of the patient based on the time-function.

16 Claims, 10 Drawing Sheets

(51) Int. Cl.
   *A61B 5/00*   (2006.01)
   *A61M 1/14*   (2006.01)
   *G06T 7/00*   (2017.01)
   *G06T 7/20*   (2017.01)
   *A61M 1/36*   (2006.01)

(52) U.S. Cl.
   CPC .............. *G06T 7/0012* (2013.01); *G06T 7/20* (2013.01); *A61B 5/7207* (2013.01); *A61B 5/7257* (2013.01); *A61B 2576/00* (2013.01); *A61M 2205/3303* (2013.01); *A61M 2205/3306* (2013.01); *G06T 2207/10024* (2013.01); *G06T 2207/10132* (2013.01); *G06T 2207/30084* (2013.01); *G06T 2207/30104* (2013.01)

(58) Field of Classification Search
   CPC .......... G06K 2009/00932; G06K 2009/00939; G06K 9/0061; G06K 9/6202; G06K 9/6289; G06K 2209/05; A61B 5/02007; A61B 5/02035; A61B 5/021; A61B 5/026–5/0275; A61B 8/06; A61B 3/1233; A61B 3/1241; A61B 5/0215; A61B 2576/00; A61M 1/3653; A61M 1/3656; A61M 1/3659; A61M 2205/3306; G01P 5/001; G01P 5/26; G06Q 50/24; G06F 19/30–19/325

See application file for complete search history.

(56) References Cited

U.S. PATENT DOCUMENTS

2009/0080757 A1   3/2009   Roger et al.
2013/0274610 A1   10/2013  Kamshilin et al.
2014/0340502 A1   11/2014  Freeman et al.

* cited by examiner

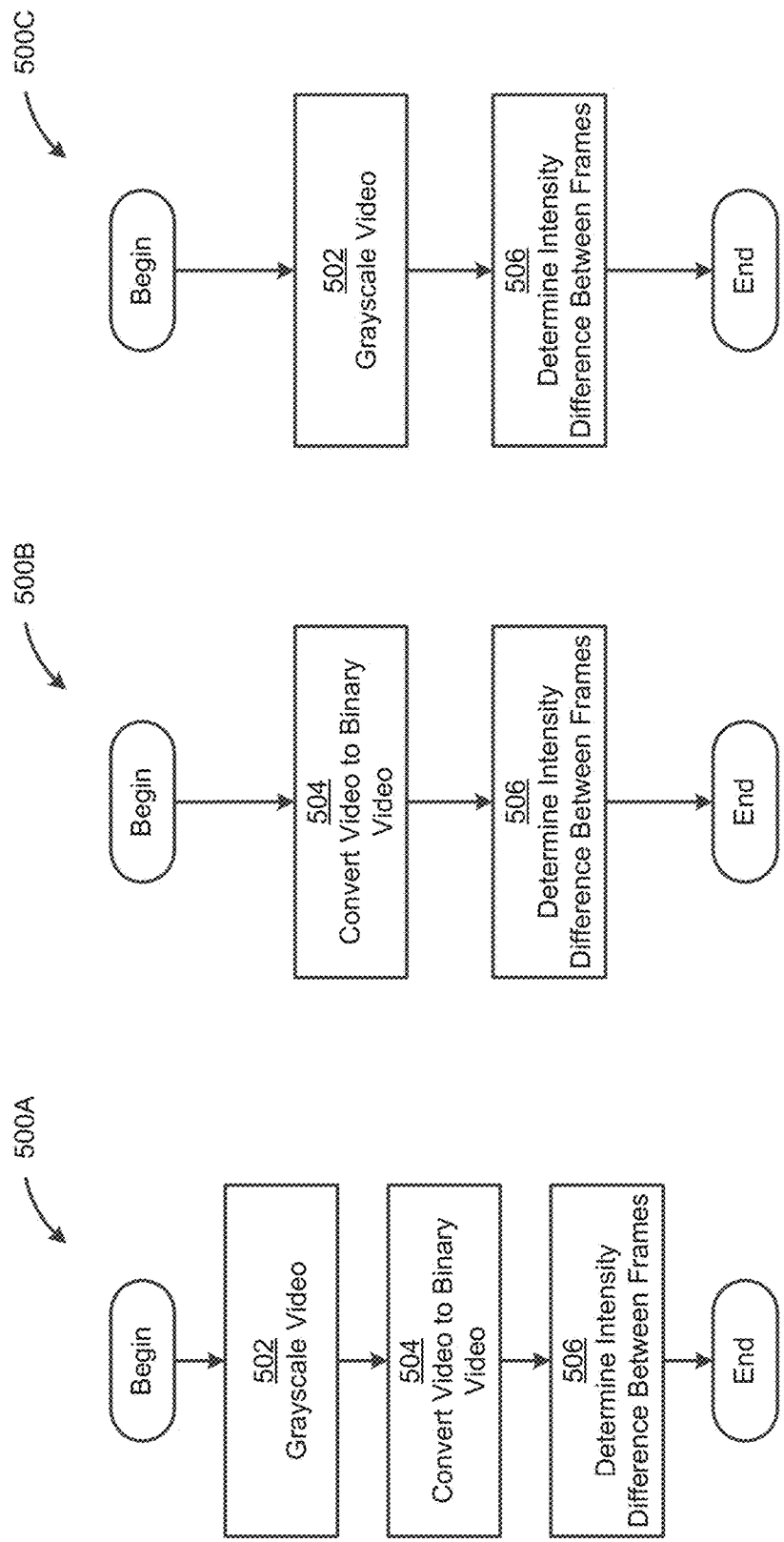

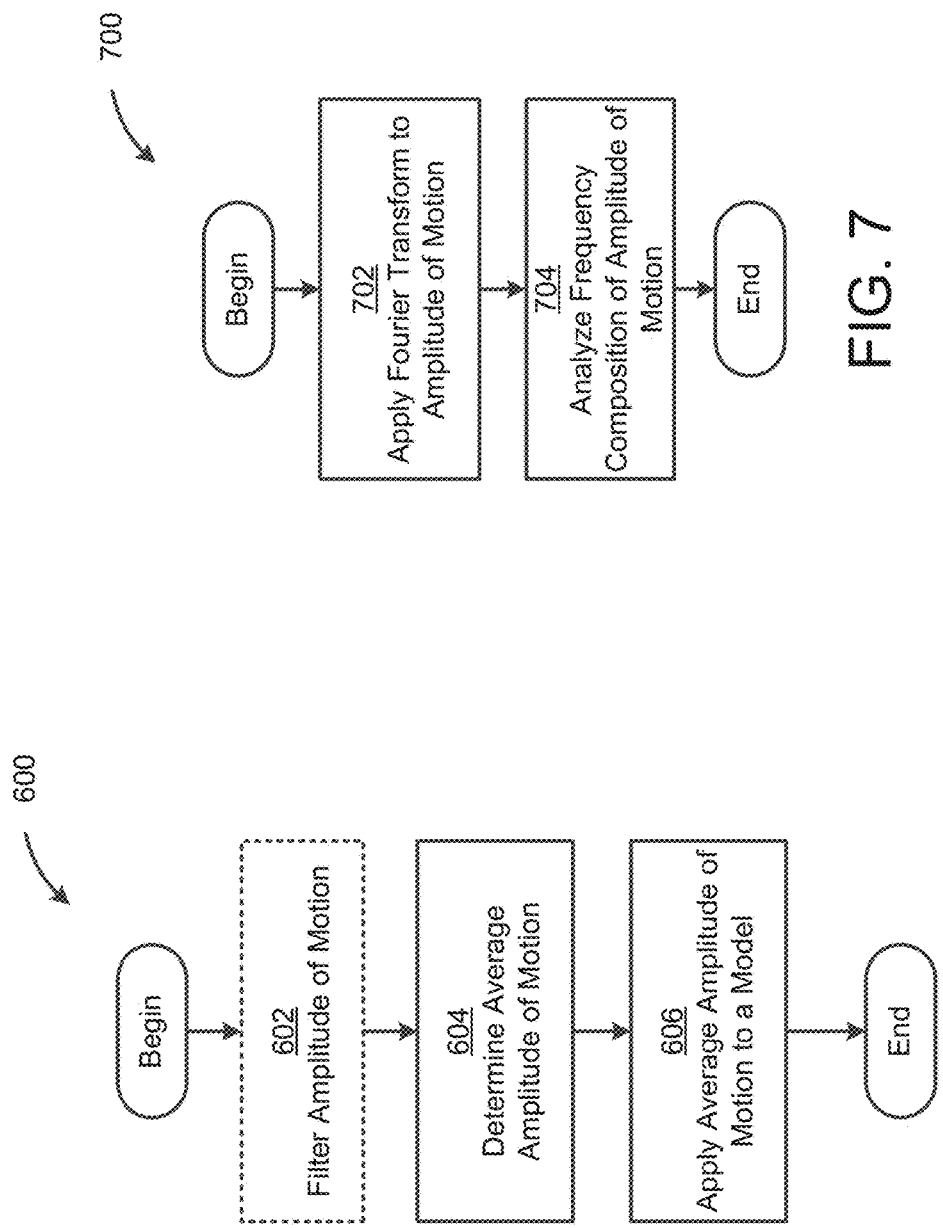

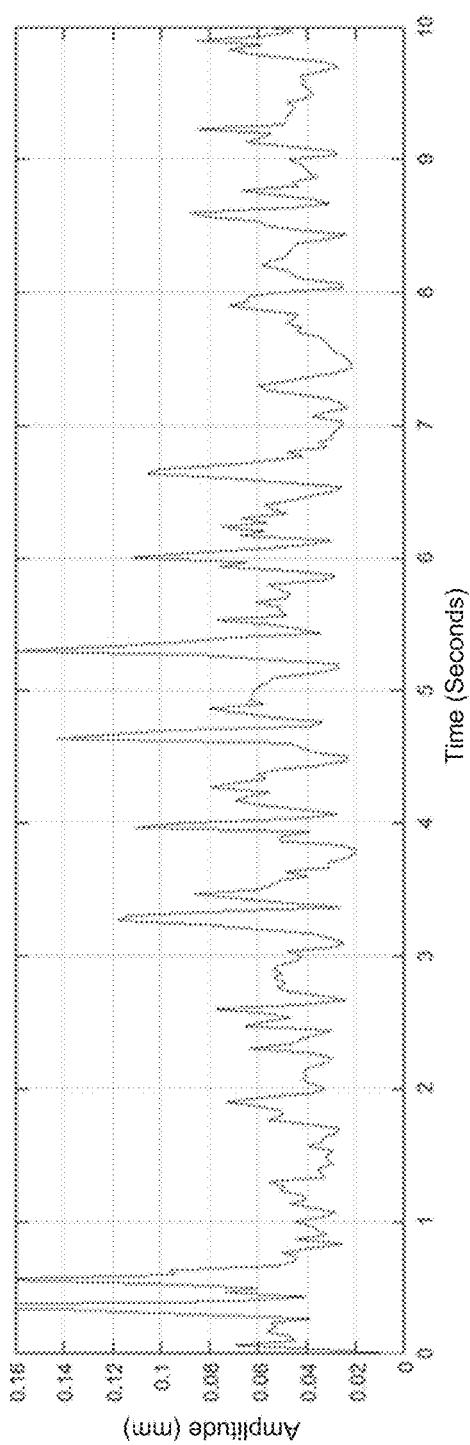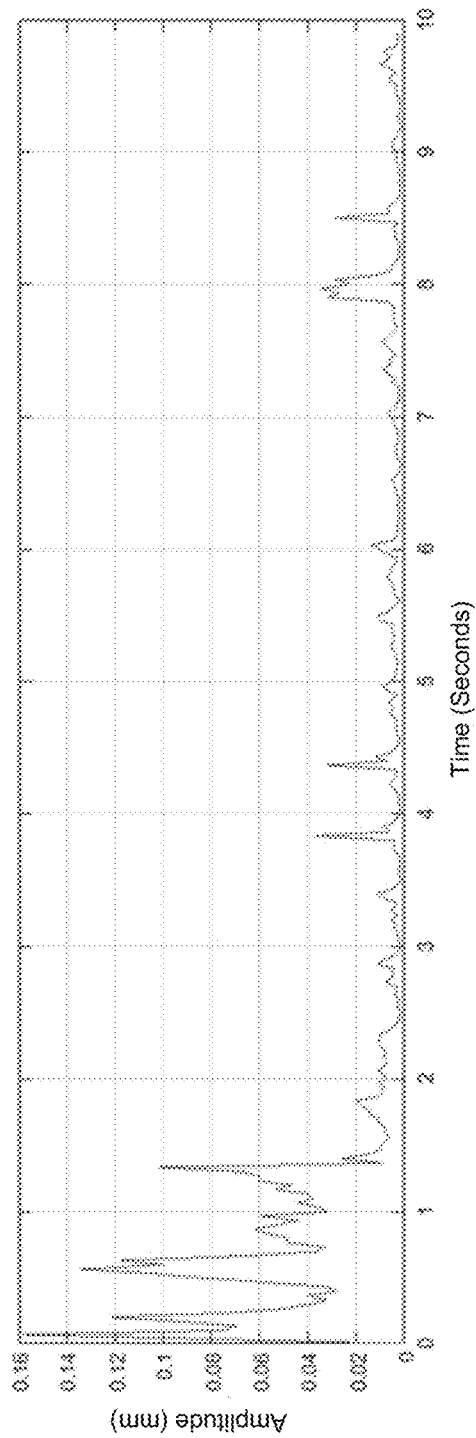
FIG. 9A
FIG. 9B

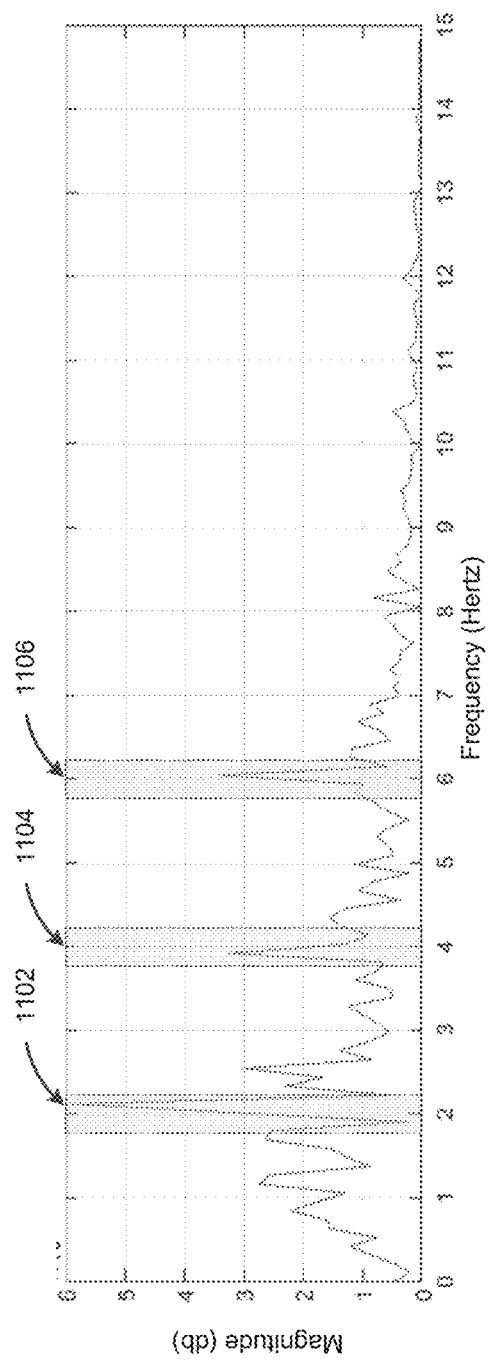
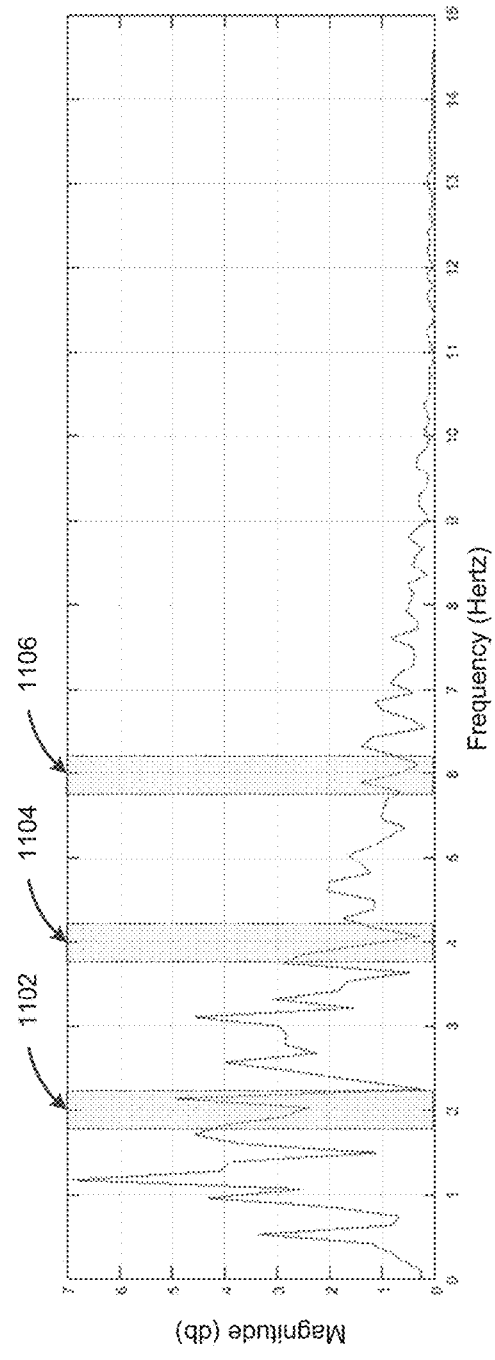
FIG. 11A
FIG. 11B

METHOD AND APPARATUS OF ASSESSMENT OF ACCESS FLOW IN HEMODIALYSIS PATIENTS BY VIDEO IMAGING PROCESSING

CROSS REFERENCE TO RELATED APPLICATIONS

This application claims priority under 35 U.S.C. § 119(e) to U.S. Provisional Application Ser. No. 62/250,294, titled "METHOD AND APPARATUS OF ASSESSMENT OF ACCESS FLOW IN HEMODIALYSIS PATIENTS BY VIDEO IMAGING PROCESSING," filed Nov. 3, 2015, which is incorporated herein by reference in its entirety.

BACKGROUND

Technical Field

The technical field of this disclosure relates generally to medical devices, and more particularly to methods and apparatus for assessing blood flow in patients.

Background Discussion

Assessment of the status of the vascular access region (e.g., a vein) in hemodialysis patients is routinely one of the most important challenges in clinical practice. Hemodialysis patients depend on the vascular access to connect to a hemodialysis machine that provides life-saving filtration of waste products from the blood stream of the patient. The vascular access of a patient, however, may fail because of blood clotting in and/or around the vascular access. Eventually, the patients who experience vascular access failure may have to undergo surgery to improve blood flow in the vascular access.

A current standard practice to access the health of the vascular access is to use Doppler ultrasound techniques to generate ultrasound images of the vascular access. In clinical practice, a physician reviews the ultrasound images of the vascular access to assess the health of the vascular access based on the physician's experience. However, there is no standard practice to obtain the ultrasound images. Accordingly, the quality of the resulting ultrasound images may be inconsistent based on, for example, the way the ultrasound probe is held against the patient and which areas of the patient are imaged. Ultrasound imaging also requires a skilled operator, is location-dependent, and is time-consuming.

Electromagnetic flowmeters have also been used, in an industrial setting, in assessing blood flow. Yet attempts to apply such techniques in a clinical practice have had limited success due to a lack of accuracy, and insensitive specific location of blood flow.

SUMMARY OF INVENTION

Aspects and examples are directed to various non-invasive techniques for assessing blood flow characteristics in patients using video image processing. The blood flow characteristics may be determined by analyzing the small motion exhibited by the skin of a patient as fluid (e.g., blood) circulates through an area of interest on the patient. The small motion may be analyzed to determine, for example, the rate of blood flow in various regions of the patient. These non-invasive techniques may be readily employed to, for example, assess the health of a vascular access in a hemodialysis patient. For example, video capturing the small motions exhibited by an arterio-venous (AV) fistula of a hemodialysis patient may be analyzed to estimate the blood flow in the vascular access of the patient. Further, the captured video may be analyzed to identify thrombosis in the patient and/or predict the onset of thrombosis. The information regarding the health of the vascular access in hemodialysis patients may be employed by physicians to intervene before the vascular access fails thereby extending the useful life of the vascular access.

According to at least one aspect, a method of analyzing at least one blood flow characteristic of a patient is provided. The method includes capturing a video including a plurality of frames of an arterio-venous (AV) fistula on the patient, amplifying motion in the video to produce a motion-amplified video, determining a difference in intensity between consecutive frames in the motion-amplified video to produce a time-function of an amplitude of optic flow representing movement in an area of interest on the patient, and determining the at least one blood flow characteristic of the patient based on the time-function.

In some examples, the act of capturing the video includes capturing monochrome video. For example, the monochrome video may be captured by a monochrome image sensor.

In some examples, the act of capturing the video includes capturing color video and the method further includes grayscaling the motion-amplified video to produce a grayscaled video. In these examples, the method may further include converting the grayscaled video to a binary video and the act of determining the difference in intensity may include determining the difference in intensity between consecutive frames in the binary video. It is appreciated that the act of determining the difference in intensity between consecutive frames may be done directly on the grayscaled video.

In some examples, the method further includes converting the motion-amplified video to a binary video and the act of determining the difference in intensity includes determining the difference in intensity between consecutive frames in the binary video. The motion amplified video before conversion to binary may be, for example, a color video.

In some examples, each of the plurality of frames includes a plurality of pixels and the act of determining the difference in intensity may include determining, pixel-by-pixel, a plurality of intensity differences between each pixel in consecutive frames. In these examples, the act of determining the difference in intensity may further include summing the plurality of pixel intensity differences.

In some examples, the at least one blood flow characteristic of the patient includes an estimated access blood flow of the patient. In these examples, the act of determining the at least one blood flow characteristic may include determining an average amplitude of the difference in intensity and applying the average difference in intensity to a model to obtain the estimated access blood flow. It is appreciated that the act of applying the average difference in intensity to the model may include applying the average difference in intensity to a lookup table. According to a further embodiment, determining the at least one blood flow characteristic of the patient based on the time-function includes determining a frequency of the motion.

According to at least one aspect, a method of analyzing vascular access blood flow in hemodialysis patients is provided. The method includes collecting a first time sequence of two-dimensional video images of an arterio-venous fistula region in the hemodialysis patient using an imaging sensor including an M×N array of pixels, performing a motion amplification process on each two-dimensional video image in the first time sequence of two-dimensional video images to produce a second time series of two-dimensional motion-amplified video images, transforming the second time series of two-dimensional motion-amplified video images into a third, one-dimensional time series of amplitudes of optic flow representing the vascular access blood flow based on a pixel-by-pixel determination of changes in intensity between consecutive two-dimensional motion-amplified video images in the second time series of two-dimensional motion-amplified video images, and estimating the vascular access blood flow based on a combination of the third, one-dimensional time series of amplitudes of optic flow and at least one clinical measurement of the vascular access blood flow.

According to at least one aspect, a method of determining a physiological parameter associated with an arterio-venous fistula in a hemodialysis patient is provided. The method includes collecting a first time series of video images of the arterio-venous fistula using an imaging sensor including an M×N array of pixels, performing a motion amplification process on each video image in the first time sequence of video images to produce a second time series of motion-amplified video images, transforming the second time series of motion-amplified video images into a third time series of amplitudes of optic flow based on a pixel-by-pixel determination of changes in intensity between consecutive motion-amplified video images in the second time series of motion-amplified video images, and determining the physiological parameter based at least in part on the third time series of amplitudes of optic flow.

According to at least one aspect, a system for determining a physiological parameter associated with an arterio-venous fistula in a hemodialysis patient is provided. The system includes an imaging assembly configured to obtain a first time series of video images of the arterio-venous fistula and a video processing assembly coupled to the imaging assembly and configured to receive and process the first time series of video images. The video processing assembly may be configured to process the first time series of video images by performing a motion amplification process on each video image in the first time series of video images to produce a second time series of motion-amplified video images, transforming the second time series of motion-amplified video images into a third time series of amplitudes of optic flow based on changes in intensity between consecutive motion-amplified video images in the second time series of motion-amplified video images, and produce an estimate of the physiological parameter based at least in part on the third time series of amplitudes of optic flow. It is appreciated that the system may further include a display coupled to the video processing assembly and configured to display at least one of the estimate of the physiological parameter and the second time series of motion-amplified video images.

According to another aspect, a medical imaging device for imaging an arterio-venous (AV) fistula of a hemodialysis patient is provided. The medical imaging device includes a housing having an opening extending therethrough, the opening being sized to accommodate an arm of the hemodialysis patient, an arm support configured to support the arm of the hemodialysis patient when the arm extends through the opening in the housing, a rotating wheel disposed within the housing and configured to rotate about the opening, a light source disposed within the housing on the rotating wheel, the light source being configured to illuminate at least a portion of the arm that is within the opening, the portion of the arm including the AV fistula, and an imaging sensor disposed within the housing on the rotating wheel and configured to produce video images of the AV fistula.

In some examples, the medical imaging device further includes a drive assembly coupled to the rotating wheel and configured to drive rotation of the rotating wheel about the opening. The drive assembly may include, for example, a driving axle coupled to the rotating wheel and a stepper motor coupled to the driving axle. In these examples, the housing may include a wheel support assembly configured to attach the rotating wheel to the driving axle and to support the rotating wheel within the housing.

In some examples, the light source maintains a constant brightness while the imaging sensor produces the video images of the AV fistula. The light source may include, for example, a light emitting diode (LED), an incandescent bulb, a fluorescent bulb, a halogen bulb, or any combination thereof. It is appreciated that, in some examples, the light source may have a configurable brightness.

In some examples, the arm support includes a first arm support section disposed on a first side of the housing and a second arm support section disposed on a second side of the housing, the second side opposing the first side, such that when the arm extends through the opening, a proximal portion of the arm is supported by the first arm support section and a distal portion of the arm is supported by the second arm support section.

In some examples, the opening has a substantially circular shape. In these examples, the housing may be a substantially circular housing and the opening may be centrally disposed within the substantially circular housing. The circular housing may be, for example, attached to and supported on a mounting platform. It is appreciated that the opening may be a shape other than circle including, for example, an oval, an ellipse, a rectangle, or a square.

In some examples, the imaging sensor includes a communications port configured to provide the video images to an external device. The external device may include, for example, an external computer system and/or a handheld device (e.g., a phone or a tablet).

In some examples, the medical imaging device further includes a controller configured to control rotation of the rotating wheel. In these examples, the medical imaging device may further include a display and wherein the controller and the display are integrated into a handheld device. The handheld device may include, for example, at least one of a mobile phone or a tablet computer. It is appreciated that the controller may be configured to control the rotation of the rotating wheel responsive to an instruction received from a user and/or control the rotation of the wheel based on an amplitude of imaged motion in the AV fistula and to rotate the rotating wheel so as to reposition the imaging sensor to maximize the amplitude of the imaged motion.

According to at least one aspect, a medical imaging system for analyzing at least one blood flow characteristic of a patient is provided. The medical imaging system includes an imaging sensor constructed to capture video comprising a plurality of frames of an arterio-venous (AV) fistula on the patient and at least one processor coupled to the imaging sensor. The at least one processor may be configured to receive the video from the imaging sensor, amplify motion in the video to produce a motion-amplified video, determine a difference in intensity between consecutive frames in the motion-amplified video to produce a time-function of an amplitude of optic flow representing movement in an area of interest on the patient, and determine the at least one blood flow characteristic of the patient based on the time-function of the amplitude of optic flow.

In some examples, the medical imaging system further includes a display coupled to at least one processor and configured to display the video. In some examples, the at least one blood flow characteristic includes at least one of an estimate of an access blood flow and a prediction of whether the patient will develop thrombosis. In other examples, the medical imaging system further includes a moving control system configured to move the imaging sensor in a direction of an orthogonal rotating area.

Still other aspects, examples, and advantages of these exemplary aspects and examples are discussed in detail below. Examples disclosed herein may be combined with other examples in any manner consistent with at least one of the principles disclosed herein, and references to "an example," "some examples," "an alternate example," "various examples," "one example" or the like are not necessarily mutually exclusive and are intended to indicate that a particular feature, structure, or characteristic described may be included in at least one example. The appearances of such terms herein are not necessarily all referring to the same example.

BRIEF DESCRIPTION OF THE DRAWINGS

Various aspects of at least one example are discussed below with reference to the accompanying figures, which are not intended to be drawn to scale. The figures are included to provide illustration and a further understanding of the various aspects and examples, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure. In the figures:

FIGS. 5A-5C are example flow diagrams of example processes for determining the amplitude of motion in the video;

FIG. 6 is a flow diagram of an example process for estimating the access blood flow (ABF) of a patient;

FIG. 7 is a flow diagram of an example process for predicting thrombosis in a patient;

FIG. 9A is a graph illustrating the intensity difference between frames in a patient with a high ABF;

FIG. 9B is a graph illustrating the intensity difference between frames in a patient with a low ABF;

FIG. 11A is a graph illustrating the frequency components of the intensity difference between frames in a patient with low ABF after physician intervention; and FIG. 11B is a graph illustrating the frequency components of the intensity difference between frames in a patient with low ABF before physician intervention.

DETAILED DESCRIPTION

Aspects and examples are directed to non-invasive techniques for assessing blood flow characteristics in patients using video image processing. These non-invasive techniques analyze the motion exhibited by the skin of a patient in an area of interest, an arterio-venous (AV) fistula for example, as blood travels through the area to provide insight regarding various blood flow characteristics of the patient. For example, the non-invasive techniques may be employed to determine the access blood flow (ABF) and/or predict the onset of thrombosis in hemodialysis patients.

It is to be appreciated that examples of the methods and apparatuses discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements, and features discussed in connection with any one or more examples are not intended to be excluded from a similar role in any other example. Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. The use herein of "including," "comprising," "having," "containing," "involving," and variations thereof is meant to encompass the items listed thereafter and equivalents thereof as well as additional items. References to "or" and "and/or" may be construed as inclusive so that any terms described using "or" and "and/or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Example Hemodialysis System

Figure 1:
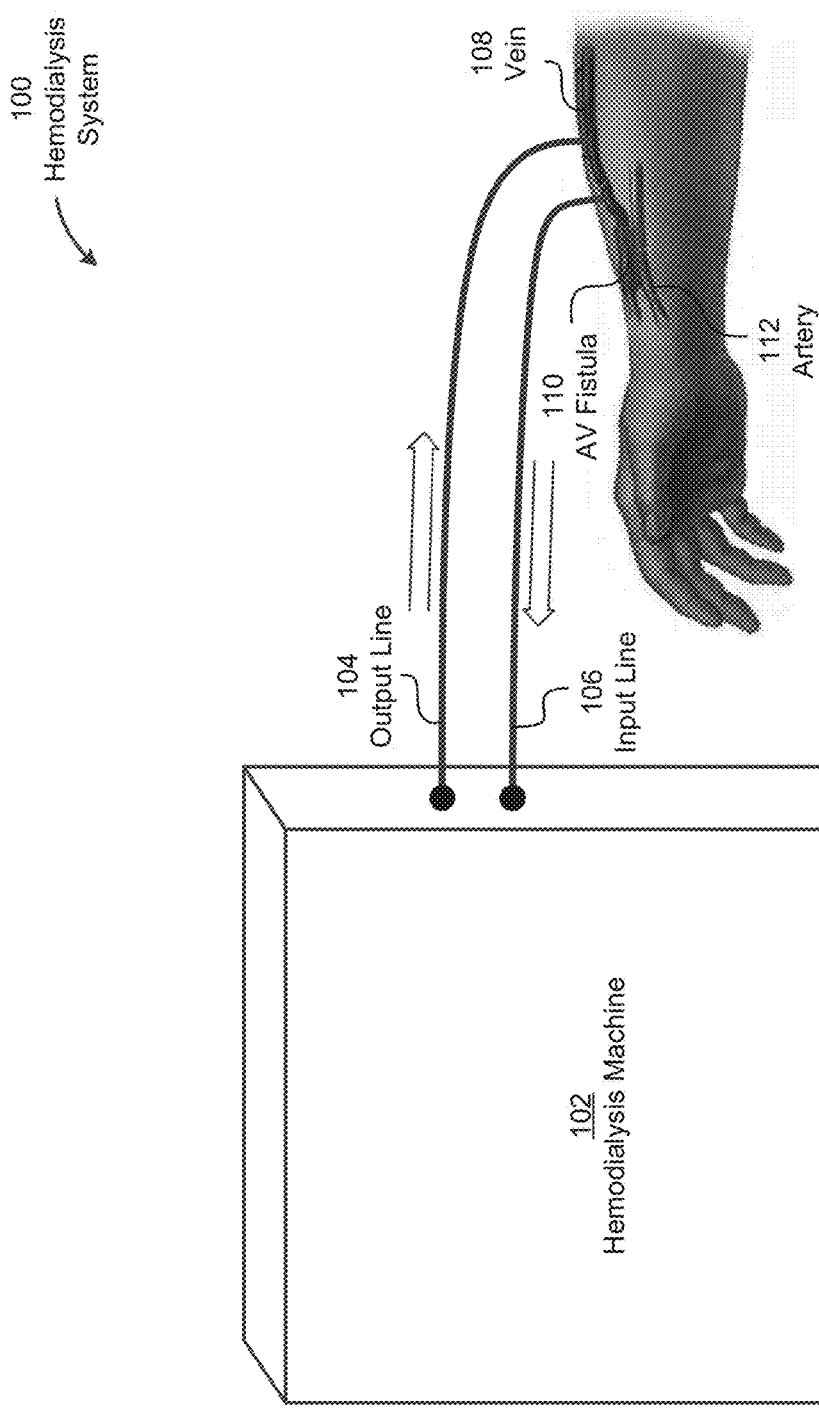
FIG. 1 is an example hemodialysis system.

Hemodialysis systems may purify the blood of a patient with improperly functioning kidneys to remove excess fluid and waste products including, for example, urea. FIG. 1 illustrates an example hemodialysis system 100 to purify the blood of a patient. As illustrated, the hemodialysis system 100 includes a hemodialysis machine 102 that purifies the blood. The blood is received by the hemodialysis machine 102 from the patient via an input line 106. The input line 106 may comprise a tube attached to a needle that may be inserted into the vascular access (e.g., the vein 108) of the patient. In order to deliver sufficient blood flow to the dialysis machine 102, a high access blood flow (ABF) may be required. A physician may increase the ABF in the vein 108 by surgically creating an arterio-venous (AV) fistula 110 by connecting an artery 112 to the vein 108. Thereby, the blood from the artery 112 may directly flow into the vein 108. The increased ABF in the vein 108 caused by the AV fistula 110 may increase the blood flow in input line 106 to the hemodialysis machine 102. After the hemodialysis machine 102 filters the blood to remove various waste products, the blood is returned to the vein 108 of the patient by an output line 104. Similar to the input line 106, the output line 104 may comprise a tube connected to a needle that may be inserted into the patient.

The AV fistula 110 that provides the high ABF for the dialysis machine may have various complications. For example, a clot may form inside the AV fistula 110, the vein 108, and/or the artery 112 and reduce the ABF in the vein 108. These complications may be mitigated by monitoring the ABF of the patient and/or predicting thrombosis (e.g., clot formation blocking blood flow) as described in more detail below. Predicting thrombosis may allow a physician to take pre-emptive action, including but not limited to repairing the AV fistula, early in the formation of the complication and thereby prolong the functional life of mature AV fistulas.

Example Methods for Monitoring Blood Flow

Figure 2:
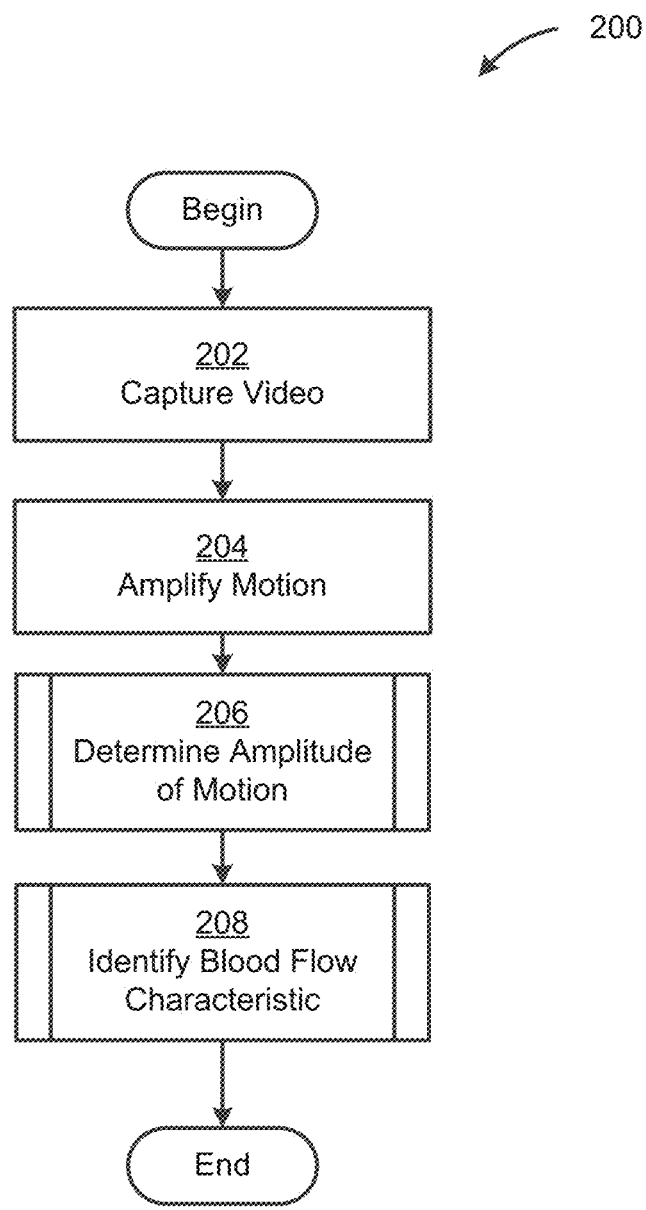
FIG. 2 is a flow diagram of an example process for monitoring access blood flow of a patient.

FIG. 2 provides an example non-invasive method of monitoring access blood flow in a patient using video image processing. The method 200 captures and analyzes images of the small motion of an area of interest (e.g., an AV fistula) to identify various access blood flow characteristics of the patient. In the case of hemodialysis patients, the access blood flow characteristics may include, for example, the ABF of the patient and/or the likelihood of the patient developing thrombosis.

In act 202, a system, such as the system described above, captures a video recording of an area of interest on the patient. For example, the system may capture video of an AV fistula of the patient, although other areas of interest are possible. The video may be captured while the patient is undergoing hemodialysis treatment or while the patient is in a static state (i.e., not currently undergoing hemodialysis treatment). The video recording of the area of interest on the patient may be taken by any of a variety of medical imaging systems as described in more detail below with reference to FIG. 3. In some examples, the medical imaging systems may be specifically constructed to take images of an AV fistula of a hemodialysis patient as illustrated in FIG. 4. These specifically constructed medical imaging systems may control the light surrounding the AV fistula to, for example, improve the quality of the captured video.

In act 204, the motion in the captured video recording is amplified. The motion exhibited by the skin based on various fluid dynamics beneath the skin may be very small. In these examples, amplifying the small motion exhibited by the skin better enables delineation between noise and motion in the video that is attributable to the movement of the skin. Any of a variety of methods may be employed to amplify the motion in the captured video. Example motion amplifications processes are described in more detail below with reference to the Example Motion Amplification section.

In act 206, the amplitude of the motion (e.g., optic flow) is determined. Quantifying the motion in the video enables the identification of patterns and/or particular characteristics of the motion. The amplitude may be determined by, for example, determining the intensity changes of each pixel between consecutive frames. Assuming the camera is fixed and the background is relatively constant, the pixels exhibiting color and/or intensity changes between images frames are generally capturing motion of the patient. These pixels may be assessed in the video stream to determine the degree of the motion present in the video stream. Various example processes to determine the amplitude of the motion are described in more detail below with references to FIGS. 5A-5C.

In act 208, access blood flow characteristics of the patient are determined based on the quantified amplitude of motion in the video stream. The access blood flow characteristics may be determined based on analyzing the amplitude of motion in the time domain and/or the frequency domain. For example, the ABF of a hemodialysis patient may be determined by calculating an average amplitude of the motion in the video stream and applying the determined average amplitude to a model as described in more detail with reference to FIG. 6. In other examples, the amplitude of the motion may be transformed into the frequency domain for analysis to, for example, predict the onset of thrombosis as described in more detail below with reference to FIG. 7.

The method of monitoring access blood flow 200 may be performed on a variety of systems depending upon the particular implementation. For example, the method may be performed by a medical imaging system that also captures video of the area of interest on the patient and/or performed on a computer system in communication with the medical imaging system as described in more detail below.

Example Medical Imaging Systems

Figure 3:
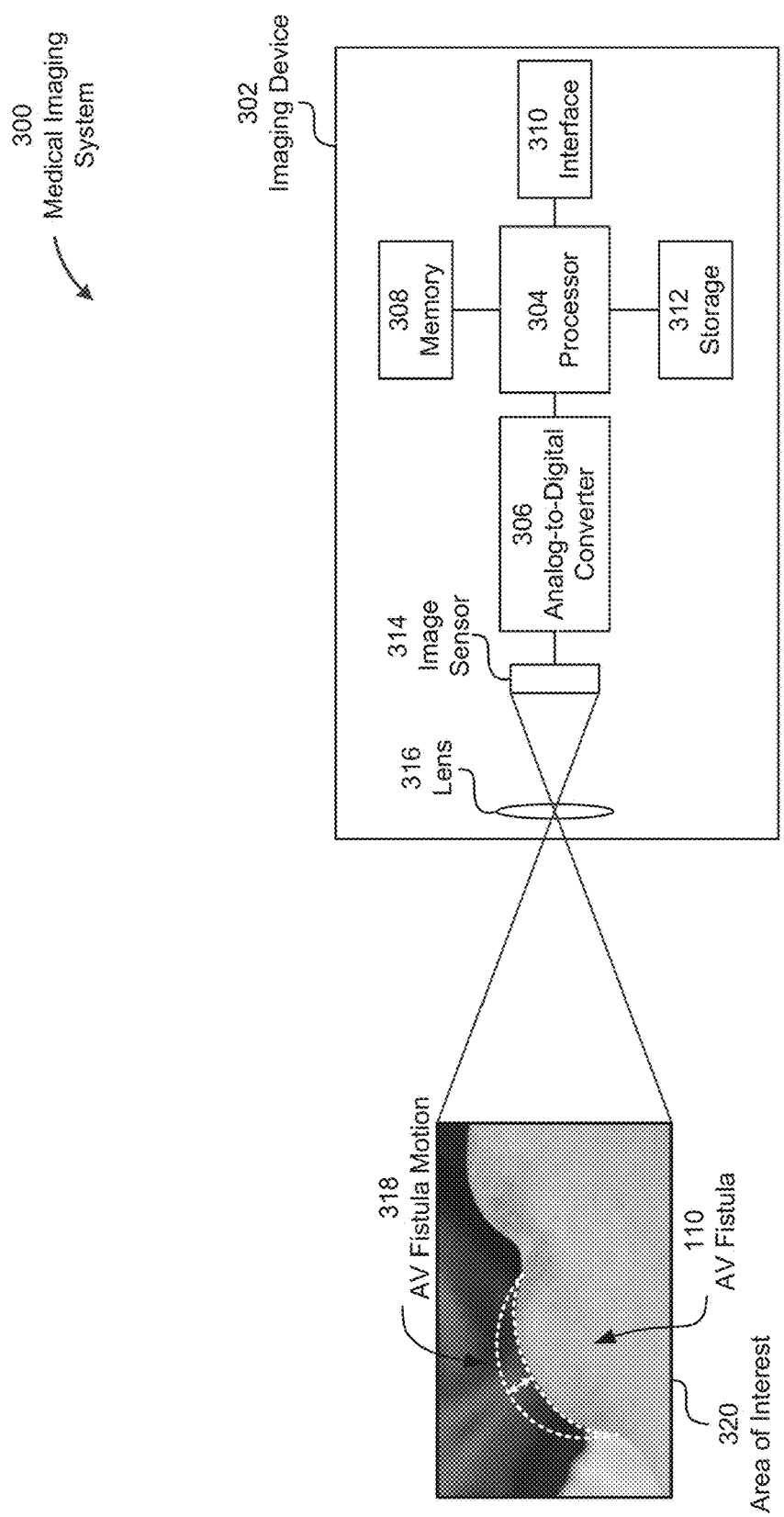
FIG. 3 is an example medical imaging system.
Figure 4:
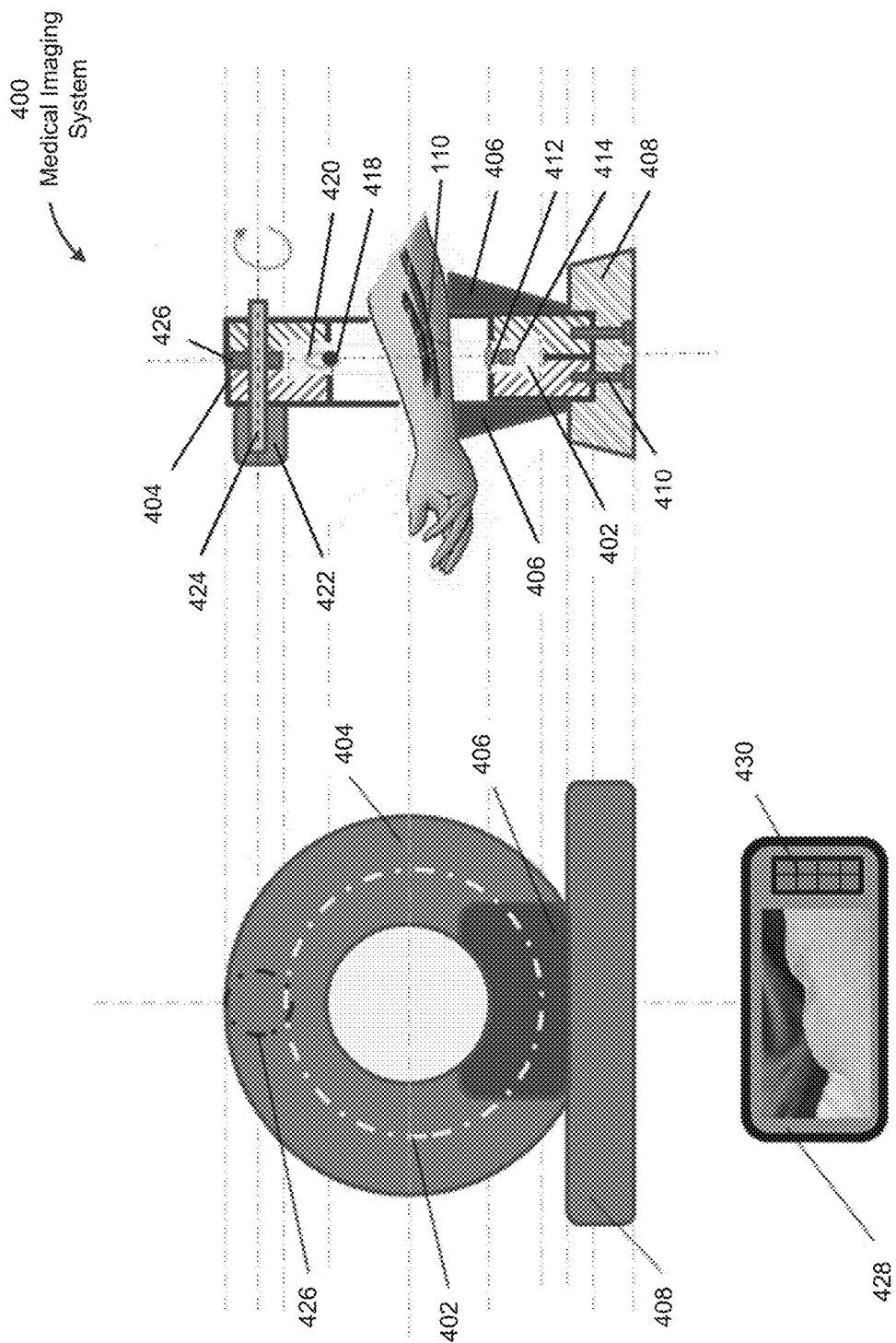
FIG. 4 is another example medical imaging system.

FIG. 3 illustrates an example medical imaging system that may capture video of an area of interest on a patient. As shown, the medical imaging system 300 includes an imaging device 302 that is configured to provide digital images and/or video frames of an area of interest 320 on a patient including, for example, an AV fistula 110. The sequence of frames in the video capture motion by the skin in the area of interest as illustrated by the AV fistula motion 318. The video may be captured by the imaging device 102 at a standard frame rate such as, for example, 30 frames per second (FPS). In other examples, the frame rate may be adjusted based on the anticipated frequency of the motion to be analyzed. For example, the frequency of the motion may be in the 0.5 to 10 Hertz (Hz) range and the frame rate may be selected to be at least double the highest frequency (i.e., 20 FPS).

As illustrated in FIG. 3, the imaging device 302 includes a processor 304 in communication with other components in the imaging device 302 to enable the acquisition of images and the organization of images into a video stream. In some examples, the processor 304 may also perform one or more acts of the method 200 of monitoring access blood flow in the patient. For example, the processor 304 may be configured to amplify the motion in the captured video consistent with act 204, determine the amplitude of motion in the video consistent with act 206, and/or identify access blood flow characteristics consistent with act 208. The processor 304 may be any type of processor, multiprocessor or controller including, for example, a digital signal processor (DSP). The processor 304 may be connected to a data storage element 312 that includes a writeable nonvolatile, or non-transitory, data storage medium in which instructions are stored that define a program, component, or other object that is executed by the processor 304. A memory 308 may also be coupled to the processor 304 to store programs and data during operation of the imaging device 302. The memory 308 may be a relatively high performance, volatile, random access memory such as a dynamic random access memory ("DRAM") or static memory ("SRAM").

The imaging device 302 may include one or more interface devices 310 connected to the processor 304 such as input devices, output devices, and combination input/output devices. These interface devices 310 may include various devices to display images and/or video to a user (e.g., a physician) and enable the user to control one or more aspects of the imaging system 300. For example, the interface 310 may include a user interface that is operable by a physician to control an aperture of the imaging device 302 and/or an orientation of the imaging device 302 relative to the area of interest 320. Example interface devices include microphones, touch screens, display screens, speakers, buttons, and keypads. It is appreciated that the interface devices 310 may also enable the processor 304 to communicate with external systems and/or devices.

The lens 316 includes one or more lenses that focus the visible radiation on the image sensor 314. It is appreciated that the lens 316 is not limited to a single physical lens as illustrated in FIG. 3. In some examples, the lens 316 includes a plurality of zoom lenses that enable optical zoom. Optical zoom may be accomplished by narrowing the field of view of the visible radiation incident on the image sensor 314.

The image sensor 314 may include a two-dimensional area of sensors (e.g., photo-detectors) that are sensitive to light. In some examples, the photo-detectors of the image sensor 314 can detect the intensity of the visible radiation in one of two or more individual color and/or brightness components. For example, the output of the photo-detectors may include values consistent with a YUV or RGB color space. It is appreciated that the image sensor 314 may be a monochrome image sensor and only capture light intensity information and not any color information. As described in more detail below, it may be advantageous in some examples to capture monochrome images to omit one or more subsequent image processing steps including, for example, any grayscaling image processing steps.

In some examples, the image sensor 314 outputs an analog signal proportional to the intensity and/or color of visible radiation striking the photo-detectors of the image sensor 314. The analog signal output by the image sensor 314 may be converted to digital data by the analog-to-digital converter 306 for processing by the processor 304. In some examples, the functionality of the analog-to-digital converter 306 is integrated with the image sensor 314.

Although the imaging device 302 is shown by way of example as one type of device upon which various aspects and functions may be practiced, aspects and functions are not limited to being implemented on the imaging device 302 as shown in FIG. 3. Various aspects and functions may be practiced on imaging devices having a different architectures or components than that shown in FIG. 3. For instance, the imaging device 302 may include specially programmed, special-purpose hardware, such as an application-specific integrated circuit ("ASIC") or a system on a chip ("SoC") tailored to perform a particular operation disclosed herein.

It is appreciated that the imaging system 300 may be specifically constructed for the purpose of capturing video of an area of interest on a patient. These dedicated devices may advantageously improve system performance by controlling the lighting of the area of interest and/or properly orientating the imaging sensor 314 and/or lens 316 at an optimum orientation relative to each other and to an area of interest to capture video of the area of interest. Such a uniquely constructed medical imaging device is illustrated in FIG. 4. The medical imaging device 400 illustrated in FIG. 4 is specifically constructed to capture images of an AV fistula on an arm of a hemodialysis patient. The medical imaging system 400 provides support for the arm of the patient to encourage the patient to remain still during the imaging process and allows a user (e.g., a physician or a technician) to control an orientation of the imaging sensor.

As illustrated in FIG. 4, the medical imaging system 400 includes a rotating wheel 402 that rotates within a housing 404 having an opening to receive a forearm of the patient including an AV fistula 110. The arm of the patient may be supported by arm cushions 406 at both the front and rear sides of the housing 404. A light support 420 is mounted and/or integral to the rotating wheel 402 that supports a light source 418. The light source 418 may be selected and/or calibrated to provide a known and substantially constant illumination. Alternatively, the light source 418 may be configured to provide a controllable level of illumination. Mounting the light source 418 to the rotating wheel 402 via the light support 420 allows the position of the light source 418 to be changed. For example, a physician may adjust a location of the light source 418 to control the lighting on and/or around the AV fistula 110. Similarly, the imaging sensor 412 is supported by an image sensor support 414 that is mounted and/or integral to the rotating wheel 402. Mounting the imaging sensor 412 to the rotating wheel 402 allows a user (e.g., a physician) to move the imaging sensor 412 to image difference regions from difference angles. In some embodiments, the image sensor support 414 may allow for movement of the imaging sensor 412 in one or more axes, such as along the length of the arm of the patient. The image sensor support 414 may further allow for movement of the imaging sensor 412 in a rotational manner, for example, around the patient's arm.

In some examples, the medical imaging system 400 may optimize a position of the light source 418 and/or the imaging sensor 412 to capture the highest quality video of the AV fistula 110. For example, the location may be optimized so as to yield the largest detected amplitude of motion of the AV fistula 110. In some examples, this orientation is such that the motion of the AV fistula is substantially in the plane captured by the imaging sensor. It has been determined, for example, that the medical imaging system 400 may provide optimal results when the imaging sensor 412 is at a position approximately 30 centimeters away from the AV fistula 110, and at an angle capturing a lateral view of the AV fistula 110.

The housing 404 may be connected to a base 408 by screws 410 to keep the medical imaging system 400 in place on a flat surface (e.g., a table). It is appreciated that other mechanisms may be employed to connect the base 408 to the housing 404. For example, the base 408 may be constructed to be integral to the housing 404.

The rotating wheel 402 may be turned by a variety of mechanisms. For example, the rotating wheel 402 may be connected to a driving gear 426 that is powered by a motor 422 via a driving axle 424. The motor 422 may be, for example, a stepper motor that receives instructions from another device. For example, the user interface device 428 may include a keypad 430 that may be operated by a user (e.g., a physician) to control the rotation of the rotating wheel 402. In some examples, the user can view the current position of the imaging sensor 412 on a display integrated into the user interface device 428. The user interface device 428 may take a variety of forms and may be integral to the medical imaging system 400 or in wireless communication with the medical imaging system 400. For example, the user interface device 428 may be a smartphone, tablet, or computer in wireless communication with the medical imaging system 400.

It is appreciated that various medical imaging systems may be constructed in a variety of forms based on, for example, the particular area of interest being imaged. Further, any of these medical imaging systems may perform one or more additional functions separate from capturing video of the area of interest as described above. For example, the medical imaging systems may amplify the motion in the captured video consistent with act 204 of the blood flow monitoring process 200.

Example Motion Amplification Techniques

The motion exhibited by, for example, an AV fistula may be difficult (or impossible) to see with a human eye from raw image data. These small motions may be amplified to increase the scale of the motion to simplify the delineation between noise and movement in the video. The motion amplification may be achieved by, for example, performing eulerian video magnification on the captured video. Eulerian video magnification combines spatial and temporal processing to amplify subtle motion in the video.

In eulerian video magnification, the video sequence is decomposed into different spatial frequency bands using a Lapancian pyramid. After decomposing the signal into different spatial frequency bands, temporal filters may be applied to select frequencies of interest within the spatially decomposed frequency bands. The frequencies of interest may include, for example, a range surrounding the normal heart rate of a human.

The selected frequencies of interest may be amplified and recombined with the respective spatial frequency bands. Thereby, motion within the frequencies of interest is amplified. These spatial frequency bands may be recombined to form a new motion amplified video. Additional examples regarding eulerian video magnification are provided in U.S. Patent Application Publication No. 2014/0072190 titled "LINEAR-BASED EULERIAN MOTION MODULATION," published on Mar. 13, 2014, which is hereby incorporated herein by reference in its entirety.

It is appreciated that other methods may be employed to amplify the motion in the captured video. In addition, one or more processes may be employed to crop the video to remove areas in the video frames that are not exhibiting any motion (e.g., background) to, for example, reduce the computational complexity of the subsequent quantification of the motion in the video as described below.

Example Motion Quantification Techniques

The amplified motion in the captured video may be quantified in order to analyze the motion. The motion in the images may be quantified by analyzing changes in the intensity of light between successive frames in an image. Given a still video recording device and a still scene behind the area of interest on the patient, the intensity of light should be relatively constant at all areas not exhibiting any motion (e.g., a floor in the background of a video). The areas with motion in the video exhibit changes in intensity as the pixels change from illustrating the background to illustrating the skin of the patient. For example, the AV fistula may be imaged against a still backdrop (e.g., a hospital floor or wall). As the AV fistula expands and contracts, various pixel locations switch between being the constant floor color with the color the skin of the patient in the video sequence. Identifying the number of pixels that are exhibiting these changes provides a benchmark to identify how much motion is being captured in the video. Process 500A in FIG. 5A illustrates such an example method of quantifying the motion.

Referring to act 502 in FIG. 5A, the motion amplified video is grayscaled to, for example, combine the plurality of color channels of the video frames into a single luminance channel. Any of a variety of methods may be employed to grayscale the motion amplified video as is known by those skilled in the art. For example, the motion amplified video may be grayscaled by taking a weighted average of the various color channels (e.g., R, G, and B channels). It is appreciated that act 502 may be omitted in certain circumstances, for example, applications where the video recording is taken with a monochrome imager as illustrated by process 500B in FIG. 5B.

In act 504, the motion amplified and grayscaled video is converted to a binary video with each pixel being either black or white. The grayscaled video may be converted to binary by, for example, applying a threshold to each pixel in the frames. For example, each pixel value in the grayscaled video may be an 8-bit value between 0 and 255 representing an intensity between white (e.g., 0) and black (e.g., 255). In this example, a threshold of 125 may be applied that converts all of the pixels with a value above 125 to black and converts all pixels with a value below 125 to white. The threshold applied to the grayscaled video may be, for example, a pre-programmed value and/or determined dynamically by the system. For example, the system may analyze a tonal distribution of the successive frames to identify a particular threshold. It is appreciated that a color image may be directly converted into a binary image and, in some examples, the intermediary step of grayscaling the image may be omitted as illustrated by process 500B in FIG. 5B.

In act 506, the system determines the intensity changes between successive frames in the binary video. The intensity changes may be determined by identifying a difference in intensity values between each respective pixel in successive frames and summing the differences. For example, the intensity I at any given pixel location in the $i^{th}$ frame with m by n pixel locations in the video stream A may be represented by equation (1) below:

$$I(m,n,t)=A_i(m,n) \quad (1)$$

The difference in intensity I at each respective pixel location may be determined. For example, the pixel location (3, 4) may have a value of 0 in a first frame and have a value of 1 in a second subsequent frame thereby yielding a difference of 1. An example equation illustrated the intensity changes for each pixel between frames is illustrated by equation (2):

$$\Delta I(m,n,t)=A_{i+1}(m,n)-A_i(m,n) \quad (2)$$

The determined intensity changes between each respective pixel in successive frames may be combined to form a single array of values. For example, each element in the array may be a sum of the differences between respective pixel values in two successive frames. An example equation illustrating the summation of intensity changes across entire frames is illustrated by equation (3) below.

$$\Delta I(t)=\Sigma_{n=1}^{N}\Sigma_{m=1}^{M}(A_{i+1}(m,n)-A_i(m,n)) \quad (3)$$

The array of intensity changes may be represented as a time function. The units of the time function of intensity changes may be converted based on the particular implementation. For example, the time function may be converted from changing pixels per consecutive frame pair to millimeters of displacement of the skin.

It is appreciated that the determination of intensity changes performed in act 506 does not need to be performed on a binary video stream. The determination of intensity changes described above may also be readily applied to, for example, a grayscaled video stream as illustrated by process 500C in FIG. 5C. For example, the intensity differences determined for a given pixel in two successive frames may shift from a first range of −1 to 1 in the case of binary video stream to a second range of −255 to 255 for 8-bit grayscaled video stream.

Example Blood Flow Characteristic Identification Techniques

The quantified amplitude of motion in successive frames of the captured video may be analyzed to determine various blood flow characteristics of the patient. These blood flow characteristics may be determined based on various patterns in the amplitude of motion exhibited by patients with low and high ABFs. For example, the ABF of the patient may be estimated by determining the average amplitude of the motion as illustrated by process 600 in FIG. 6.

In optional act 602, the quantified amplitude of motion may be filtered to remove excess noise. For example, the motion of interest may have a limited possible range of frequency values. Accordingly, signal components with frequency values above the range of interest are likely noise and may be excluded. In the case of imaging an AV fistula, the range of interest may be between 0.02 Hz and 5 Hz and a bandpass filter may be constructed that attenuates signal components below 0.02 Hz and above 5 Hz. It is appreciated that the bandpass filter may be implemented in a variety of fashions as is known to those skilled in the art.

Figure 10A:
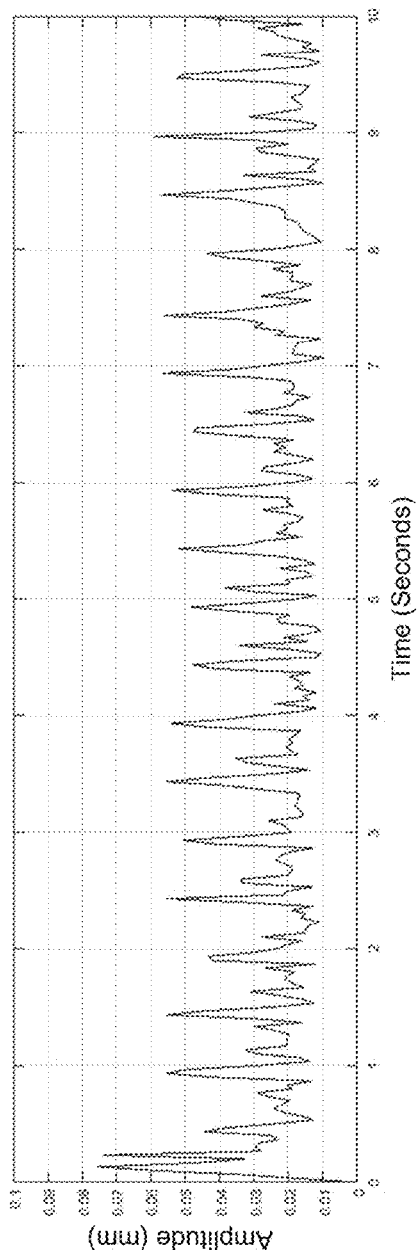
FIG. 10A is a graph illustrating the intensity difference between frames in a patient with low ABF after physician intervention.
Figure 10B:
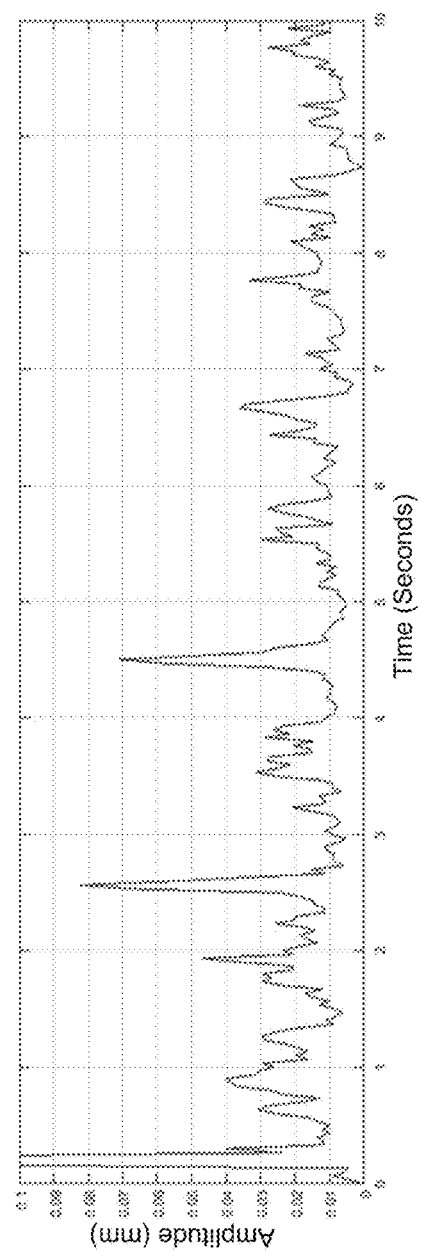
FIG. 10B is a graph illustrating the intensity difference between frames in a patient with low ABF before physician intervention.

In act 604, the average amplitude of the motion over a time duration (e.g., 10 seconds) may be determined. The averaged amplitude over the time duration may be used to determine an estimate of ABF in the patient. As illustrated by FIG. 9A showing the amplitude of motion for a patient with a high ABF and FIG. 9B illustrating the amplitude of motion for a patient with a low ABF, the amplitude of motion in the high ABF patient is generally much higher over the ten second period than the patient with the low ABF. Similarly, FIG. 10A illustrates the amplitude of motion for a patient with a low ABF after intervention by a physician to improve the blood flow and FIG. 10B illustrates the amplitude of motion of the same patient before physician intervention. As illustrated, the average amplitude of the motion generally increased after the physician intervened and blood flow improved.

In some examples, an estimate of the ABF may be determined by applying a linear (or non-linear) model to the averaged amplitude of motion over the time duration. For example, the model may be a linear model characterized by equation 4 below.

$$ABF = A * \text{Average Amplitude} + B \quad (4)$$

Figure 8:
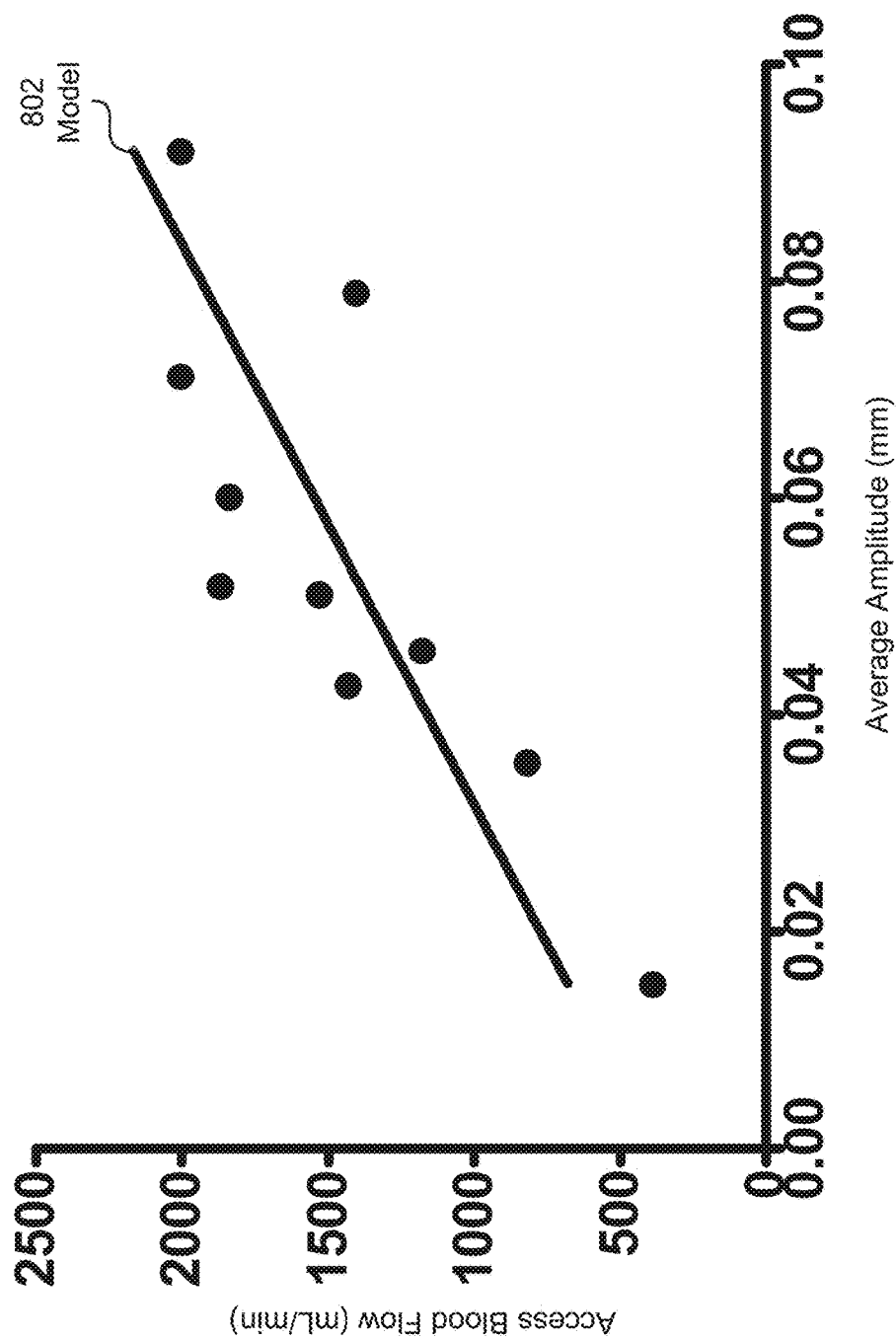
FIG. 8 is a graph illustrating the relationship between the intensity difference between frames and the ABF in a patient.

In the model illustrated by equation 4, the coefficient A and the constant B may be determined based on, for example, a linear regression analysis of experimental data obtained from a set of patients. The coefficient A and the constant B also could be the functions of patients' physiological parameters, for example A and B could be associated with body composition (e.g., fat and muscle), weight, height and gender. FIG. 8 illustrates an example graph illustrating the relationship between the average amplitude over a ten second period with the ABF measured with conventional techniques (e.g., by online-clearance monitoring). As illustrated, a model 802 may be derived from the set of data to illustrate the relationship between average amplitude and estimated ABF. In the graph illustrated in FIG. 8, the model 802 has a coefficient A equal to 19666 and a constant B equal to 319.21. Once the model is generated, the model may be implemented as, for example, a look-up table that correlates average amplitude to ABF. Other models separate from the linear model illustrated in equation (4) may be employed including, for example, various non-linear models.

It is appreciated that other blood flow characteristics may be determined separate from ABF based on the amplitude of motion exhibited by the area of interest. For example, the amplitude of motion may be employed to predict thrombosis in the patient as illustrated by FIG. 7. The thrombosis prediction process 700 employs the frequency domain representation of the amplitude of motion to identify various patterns.

In act 702, a Fourier transform is applied to the time function of the amplitude of motion. Various methods may be employed to transform the time function of the amplitude of motion from the time-domain to the frequency domain including various approximation techniques as is appreciated by those skilled in the art. For example, a fast Fourier transform (FFT) may be employed to transform the time function to the frequency domain.

In act 704, the frequency composition of the amplitude of motion is analyzed. For example, the location of the peaks in the frequency domain representation of the amplitude of motion may be identified and compared to one or more threshold ranges. FIGS. 11A and 11B illustrate the comparison between a patient with low ABF before and after physician intervention to improve blood flow. More specifically, FIG. 11A illustrates the frequency domain representation of the amplitude of motion after physician intervention and FIG. 11B illustrates the frequency domain representation of the amplitude of motion before physician intervention. As illustrated by regions 1102, 1104, and 1106, the frequency domain representation of the amplitude of motion of the patient post-intervention has peaks around 2 Hz, 4 Hz, and 6 Hz. Pre-intervention, however, the frequency domain representation does not exhibit the same definitive peaks around 2 Hz, 4 Hz, and 6 Hz. This pattern, among others, may be employed to predict and/or identify thrombosis in the patient. For example, the patient may be predicted to develop thrombosis if the highest peaks in the frequency domain representation of the average amplitude are below the 2 Hz, 4 Hz, and 6 Hz ranges illustrated in FIGS. 11A and 11B. Thus, aspects and examples provide non-invasive procedures by which to analyze ABF in hemodialysis patients and/or predict potential physiological abnormalities, such as thrombosis, for example.

Having described above several aspects of at least one example, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. A medical imaging device for imaging an arteriovenous (AV) fistula of a hemodialysis patient comprising:
    a housing having an opening extending therethrough, the opening being sized to accommodate an arm of the hemodialysis patient;
    an arm support configured to support the arm of the hemodialysis patient when the arm extends through the opening in the housing;
    a rotating wheel disposed within the housing and configured to rotate about the opening;
    a light source disposed within the housing on the rotating wheel, the light source being configured to illuminate at least a portion of the arm that is within the opening, the portion of the arm including the AV fistula; and an imaging sensor disposed within the housing on the rotating wheel and configured to produce video images of the AV fistula.

2. The medical imaging device of claim 1, further comprising a drive assembly coupled to the rotating wheel and configured to drive rotation of the rotating wheel about the opening.

3. The medical imaging device of claim 2, wherein the drive assembly includes a driving axle coupled to the rotating wheel and a stepper motor coupled to the driving axle.

4. The medical imaging device of claim 3, wherein the housing includes a wheel support assembly configured to attach the rotating wheel to the driving axle and to support the rotating wheel within the housing.

5. The medical imaging device of claim 1, wherein the light source maintains a constant brightness while the imaging sensor produces the video images of the AV fistula.

6. The medical imaging device of claim 1, wherein the light source has a configurable brightness.

7. The medical imaging device of claim 1, wherein the arm support includes a first arm support section disposed on a first side of the housing and a second arm support section disposed on a second side of the housing, the second side opposing the first side, such that when the arm extends through the opening, a proximal portion of the arm is supported by the first arm support section and a distal portion of the arm is supported by the second arm support section.

8. The medical imaging device of claim 1, wherein the opening has a substantially circular shape.

9. The medical imaging device of claim 8, wherein the housing is a substantially circular housing and the opening is centrally disposed within the substantially circular housing.

10. The medical imaging device of claim 9, further comprising a mounting platform, the circular housing being attached to and supported on the mounting platform.

11. The medical imaging device of claim 1, wherein the imaging sensor includes a communications port configured to provide the video images to an external device.

12. The medical imaging device of claim 1, further comprising a controller configured to control rotation of the rotating wheel.

13. The medical imaging device of claim 12, further comprising a display, and wherein the controller and the display are integrated into a handheld device.

14. The medical imaging device of claim 13, wherein the handheld device includes at least one of a mobile phone or a tablet computer.

15. The medical imaging device of claim 12, wherein the controller is configured to control the rotation of the rotating wheel responsive to an instruction received from a user.

16. The medical imaging system of claim 12, wherein the controller is configured to:
  control the rotation of the rotating wheel based on an amplitude of imaged motion in the AV fistula; and
  rotate the rotating wheel so as to reposition the imaging sensor to maximize the amplitude of the imaged motion.

\* \* \* \* \*